United States Patent [19]
Jurd

[11] 3,946,047
[45] Mar. 23, 1976

[54] ALKYLCINNAMYLPHENOLS AS MOSQUITO LARVICIDES

[75] Inventor: Leonard Jurd, Berkeley, Calif.

[73] Assignee: The United States of America as represented by the Secretary of Agriculture, Washington, D.C.

[22] Filed: Feb. 27, 1975

[21] Appl. No.: 554,057

[52] U.S. Cl. ............................................... 424/346
[51] Int. Cl.² ........................................... A01N 9/26
[58] Field of Search ................................... 424/346

[56] References Cited
UNITED STATES PATENTS

| | | | |
|---|---|---|---|
| 3,745,222 | 7/1973 | Jurd et al. | 424/346 |
| 3,775,541 | 11/1973 | Jurd et al. | 424/346 |

*Primary Examiner*—Jerome D. Goldberg
*Assistant Examiner*—Allen J. Robinson
*Attorney, Agent, or Firm*—M. Howard Silverstein; William Takacs; Max D. Hensley

[57] ABSTRACT

Alkylcinnamylphenols, wherein the alkyl group contains 3–4 carbon atoms, are used as mosquito larvicides.

2 Claims, No Drawings

ALKYLCINNAMYLPHENOLS AS MOSQUITO LARVICIDES

DESCRIPTION OF THE INVENTION

The invention relates to and has among its objects the provision of novel methods for destroying mosquito larvae. Further objects of the invention will be evident from the following description wherein parts and percentages are by weight unless otherwise specified. The abbreviation ppm. used herein refers to parts per million. The symbol $\phi$ is used herein to represent the phenyl ( 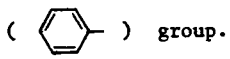 ) group.

One of the ways of controlling insect populations is to kill the insect larvae. Generally, a larvicide is applied to the breeding places or habitat of the insects where it destroys the larvae.

I have discovered that certain compounds are effective as mosquito larvicides. When the compounds of the invention are applied in larvicidal amount to the habitat of the mosquito, the larval population is substantially reduced.

The compounds used in accordance with the invention are those alkylcinnamylphenols which have the structure -

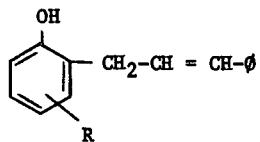

wherein R is an alkyl group containing 3 to 4 carbon atoms. Particularly preferred for the purpose of the invention is 4-t-butyl-2-cinnamyl phenol, which has the structure -

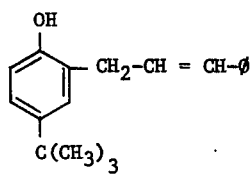

The compounds of the invention are highly effective in killing mosquito larvae. Generally, for such purpose, the compounds are applied to the breeding places of the mosquito in a concentration of about 5–15 ppm. Because the compounds are effective in very minor concentrations, it is preferred that they be dissolved or suspended in an appropriate carrier prior to application to the breeding centers. The solution or suspension increases the bulk and thus allows small amounts of the compounds to be administered to the mosquito's habitat. Preferred carriers for this purpose are volatile solvents such as acetone, ethyl ether, ethanol, benzene, xylene, and the like.

The compounds of the invention may be prepared by methods known in the art. Typically, a mixture of the appropriate alkylphenol and cinnamyl alcohol in aqueous formic acid is refluxed whereby to produce the desired alkylcinnamyl phenols. The systhesis of 4-t-butyl-2-cinnamyl phenol by this procedure is disclosed by Jurd et al., Tetrahedron, Vol. 29, pages 2347 to 2353 (1973).

EXAMPLE

The invention is further demonstrated by the following illustrative example.

A solution of 4-t-butyl-2-cinnamylphenol in acetone was prepared. The solution was added to water in such amount that the final concentration of 4-t-butyl-2-cinnamylphenol in the water was 10 ppm. Early fourth-instar larvae of *Anopheles quadrimaculatus* Say were exposed to the treated water and mortality was determined after 24 hours of exposure. It was found that 96 percent of the larvae exposed were killed.

For purpose of comparison the above test was carried out with several cinnamylphenols not included within the scope of the invention. All of them were applied at a concentration of 10 ppm. It was found that all of these compounds were ineffective, that is, the mortality obtained was less than 20 percent. The compounds so tested were: 2-methyl-4-cinnamylphenol, 4-cinnamylphenol, 4-methoxy-2-cinnamylphenol, 2,5-dimethoxy-4-cinnamylphenol, 2,4-dimethoxy-5-cinnamylphenol, 4-nonyl-2-cinnamylphenol, 4-octyl-2-cinnamylphenol, 4-(2-phenyl-2-propyl)-2-cinnamylphenol, 2-t-butyl-4-cinnamylphenol, 2-i-propyl-5-methyl-4-cinnamylphenol, and 4-t-pentyl-2-cinnamylphenol.

Having thus described my invention, I claim:
1. A method of killing mosquito larvae which comprises applying to said larvae a larvicidal amount of a compound of the formula

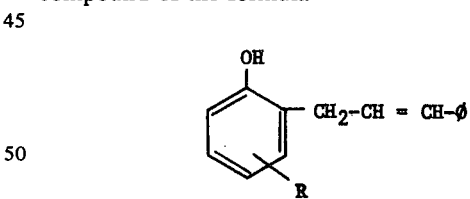

wherein R is alkyl containing 3 to 4 carbon atoms.
2. The process of claim 1 wherein the compound is 4-t-butyl-2-cinnamylphenol.

* * * * *